(12) United States Patent
Scholz et al.

(10) Patent No.: US 9,074,223 B2
(45) Date of Patent: Jul. 7, 2015

(54) VECTORS AND METHODS FOR TRANSDUCING B CELLS

(75) Inventors: Matthew Rein Scholz, Seattle, WA (US); Eric J. Herbig, Seattle, WA (US)

(73) Assignee: Immusoft Corporation, Seattle, WA (US)

(*) Notice: Subject to any disclaimer, the term of this patent is extended or adjusted under 35 U.S.C. 154(b) by 12 days.

(21) Appl. No.: 13/520,921

(22) PCT Filed: Jan. 7, 2011

(86) PCT No.: PCT/US2011/020578
§ 371 (c)(1),
(2), (4) Date: Feb. 15, 2013

(87) PCT Pub. No.: WO2011/085247
PCT Pub. Date: Jul. 14, 2011

(65) Prior Publication Data
US 2013/0143267 A1    Jun. 6, 2013

Related U.S. Application Data

(60) Provisional application No. 61/293,522, filed on Jan. 8, 2010.

(51) Int. Cl.
| | | |
|---|---|---|
| *C12P 21/04* | (2006.01) | |
| *C12P 21/06* | (2006.01) | |
| *C12N 15/63* | (2006.01) | |
| *C12N 15/86* | (2006.01) | |
| *C12N 15/867* | (2006.01) | |
| *C07K 16/00* | (2006.01) | |

(52) U.S. Cl.
CPC .............. *C12N 15/867* (2013.01); *C07K 16/00* (2013.01); *C07K 2317/14* (2013.01); *C12N 15/86* (2013.01); *C12N 2740/16043* (2013.01); *C12N 2740/16045* (2013.01); *C12N 2760/18422* (2013.01); *C12N 2810/6072* (2013.01)

(58) Field of Classification Search
CPC ................ C12N 15/86; C12N 15/867; C12N 2740/16043; C12N 2740/16045; C12N 2760/18422; C12N 2810/6072; C07K 16/00; C07K 2317/14
USPC ................................. 435/69.1, 69.6, 455, 456
See application file for complete search history.

(56) References Cited

U.S. PATENT DOCUMENTS

2003/0203489 A1    10/2003    Yonemitsu et al.

FOREIGN PATENT DOCUMENTS

WO    2008/037458 A2    4/2008

OTHER PUBLICATIONS

Phogat et al., 2011, US 20110123556 A1, effective filing date Nov. 24, 2009.*
Gorecki, D., 2001, Expert Opin. Emerging Drugs, 6(2): 187-198.*
Cao et al., 2010, Clinical and Experimental Pharmacology and physiology, vol. 37, p. 108-114.*
Takahashi et al., 2012, Frontiers in Bioscience, vol. S4, p. 133-141.*
Kaur et al., 2009, Current Gene Therapy, vol. 9. p. 434-458.*
Luo et al., 2010, US 20100203630 A1, effective filing, Nov. 21, 2008.*
Bovia et al., "Efficient transduction of primary human B lymphocytes and nondividing myeloma B cells with HIV-1-derived lentiviral vectors," *Blood* 101(5):1727-1733, Mar. 1, 2003.
Buchholz et al., "Lentiviral vectors with measles virus glycoproteins—dream team for gene transfer?" *Trends in Biotechnology* 27(5):259-265, 2009.
Fluckiger et al., "In Vitro Reconstitution of Human B-Cell Ontogeny: From CD34+ Multipotent Progenitors to Ig-Secreting Cells," *Blood* 92(12):4509-4520, Dec. 15, 1998.
Frecha et al., "Advances in the Field of Lentivector-based Transduction of T and B Lymphocytes for Gene Therapy," *Molecular Therapy* 18(10):1748-1757, Oct. 2010.
Frecha et al., "Efficient and stable transduction of resting B lymphocytes and primary chronic lymphocytic leukemia cells using measles virus gp displaying lentiviral vectors," *Blood* 114(15):3173-3180, Oct. 8, 2009.
Frecha et al., "Stable transduction of quiescent T cells without induction of cycle progression by a novel lentiviral vector pseudotyped with measles virus glycoproteins," *Blood* 112(13):4843-4852, Dec. 15, 2008.
Funke et al., "Pseudotyping lentiviral vectors with the wild-type measles virus glycoproteins improves titer and selectivity," *Gene Therapy* 16:700-705, 2009.
Funke et al., "Targeted Cell Entry of Lentiviral Vectors," *Molecular Therapy* 16(8):1427-1436, Aug. 2008.
Garvin et al., "Structure of the Murine *lck* Gene and Its Rearrangement in a Murine Lymphoma Cell Line," *Molecular and Cellular Biology* 8(8):3058-3064, Aug. 1988.
Gundersen et al., "Tissue-specific methylation of a CpG island in transgenic mice," *Gene* 113:207-214, 1992.
Luo et al., "Engineering human hematopoietic stem/progenitor cells to produce a broadly neutralizing anti-HIV antibody after in vitro maturation to human B lymphocytes," *Blood* 113(7):1422-1431, Feb. 12, 2009.
Maurice et al., "Efficient gene transfer into human primary blood lymphocytes by surface-engineered lentiviral vectors that display a T cell-activating polypeptide," *Blood* 99(7):2342-2350, Apr. 1, 2002.
Naldini et al., "In Vivo Gene Delivery and Stable Transduction of Nondividing Cells by a Lentiviral Vector," *Science* 272:263-267, Apr. 12, 1996.
Takadera et al., "Structure of the Two Promoters of the Human *lck* Gene: Differential Accumulation of Two Classes of *lck* Transcripts in T Cells," *Molecular and Cellular Biology* 9(5):2173-2180, May 1989.
Yee et al., "The regulation of myogenin gene expression during the embryonic development of the mouse," *Genes & Development* 7:1277-1289, 1993.

* cited by examiner

*Primary Examiner* — Shin Lin Chen
(74) *Attorney, Agent, or Firm* — Seed IP Law Group PLLC (57) ABSTRACT

The present disclosure provides compositions and methods for transducing B cells. In particular, the present disclosure provides for vectors and methods for transducing resting B cells and methods for differentiating same to express a transgene of interest.

15 Claims, 1 Drawing Sheet

VECTORS AND METHODS FOR TRANSDUCING B CELLS

CROSS REFERENCE TO RELATED APPLICATIONS

This application claims benefit under 35 U.S.C. 119(e) of U.S. Provisional Patent Application Ser. No. 61/293,522, filed Jan. 8, 2010 and entitled "VECTORS AND METHODS FOR TRANSDUCING B CELLS," where this US patent application is incorporated herein by reference in its entirety.

BACKGROUND OF THE INVENTION

1. Field of the Invention

The present disclosure relates to the genetic modification of B cells, a population of cells normally very resistant to transduction, and differentiation or activation thereof to express a protein of interest, such as a specific antibody.

2. Description of the Related Art

After leaving the bone marrow, the B cell acts as an antigen presenting cell (APC) and internalizes antigens. Antigen is taken up by the B cell through receptor-mediated endocytosis and processed. Antigen is processed into antigenic peptides, loaded onto MHC II molecules, and presented on the B cell extracellular surface to CD4+ T helper cells. These T cells bind to the MHC II/antigen molecule and cause activation of the B cell. Upon stimulation by a T cell, the activated B cell begins to differentiate into more specialized cells. Germinal center B cells may differentiate into memory B cells or plasma cells. Most of these B cells will become plasmablasts, and eventually plasma cells, and begin producing large volumes of antibodies (see e.g., *Trends Immunol.* 2009 June; 30(6): 277-285; *Nature Reviews,* 2005, 5:231-242).

The most immature blood cell that is considered a plasma cell instead of a B cell is the plasmablast. Plasmablasts secrete more antibodies than B cells, but less than plasma cells. They divide rapidly and are still capable of internalizing antigens and presenting them to T cells. A cell may stay in this state for several days, and then either die or irrevocably differentiate into a mature, fully differentiated plasma cell.

Terminally differentiated plasma cells express relatively few surface antigens, and do not express common pan-B cell markers, such as CD19 and CD20. Instead, plasma cells are identified through flow cytometry by their additional expression of CD38, CD78, the Interleukin-6 receptor and lack of expression of CD45. In humans, CD27 is a good marker for plasma cells, naive B cells are CD27−, memory B-cells are CD27+ and plasma cells are CD27++. CD38 and CD138 are expressed at high levels (See *Wikipedia, The Free Encyclopedia.*, "Plasma cell" Page Version ID: 404969441; Date of last revision: 30 Dec. 2010 09:54 UTC, retrieved Jan. 4, 2011; See also: *Trends Immunol.* 2009 June; 30(6): 277-285; *Nature Reviews,* 2005, 5:231-242; Nature Med. 2010, 16:123-129; Neuberger, M. S.; Honjo, T.; Alt, Frederick W. (2004). *Molecular biology of B cells*. Amsterdam: Elsevier. pp. 189-191; Bertil Glader; Greer, John G.; John Foerster; Rodgers, George G.; Paraskevas, Frixos (2008). *Wintrobe's Clinical Hematology, 2-Vol. Set*. Hagerstwon, Md.: Lippincott Williams & Wilkins. pp. 347; Walport, Mark; Murphy, Kenneth; Janeway, Charles; Travers, Paul J. (2008). *Janeway's immunobiology*. New York: Garland Science. pp. 387-388; Rawstron AC (May 2006). "Immunophenotyping of plasma cells". *Curr Protoc Cytom*).

Conventional pseudotype retroviruses have demonstrated insufficient infectivity of various tissues and cells. For example, a variety of stem cells including hematopoietic stem cell, and resting B and T cells can be important target cells in gene therapy or the like (Y. Hanazono, Molecular Medicine, Vol. 36, No. 7, 1999), but most of these cell types are found in a nondividing state (Abkowitz, J. L. et al., *Nat Med,* 2 (2), 190-7, 1996). In general, it is difficult to introduce genes using the retroviral vector exhibiting low infectivity against such nondividing cells.

Frecha et al. recently showed that resting T and B cells can be efficiently transduced with retroviral vectors pseudotyped with measles virus, glycoproteins, H and F, on their surface (*Blood* 2009 Oct. 8; 114(15):3173-80; *Blood* 2008 112:4843-4852). In particular, these retroviral vectors used Edmonston measles virus. This technique for modifying nondividing cells is of particular importance for gene therapy and immunotherapy. However, the ability to differentiate and activate B cells in vitro is an important step in preparing modified B cells for infusion into subjects. Activated and dividing B cells are also not easily genetically modified, thus this method may be used to transduce all types of B cells. The present disclosure provides vectors and methods for modifying and differentiating/activating B cells such that they can be used effectively in prophylactic and therapeutic applications.

The present disclosure provides this and other advantages as described in the detailed description.

BRIEF SUMMARY OF THE INVENTION

One aspect of the disclosure provides a method for expressing a nucleic acid of interest in a B cell comprising, transducing a resting B cell with a retroviral vector pseudotyped with measles virus glycoproteins, H and F, wherein said retroviral vector comprises the nucleic acid of interest operably linked to a promoter; and contacting the transduced resting B cells with a composition comprising CD40L in combination with a B cell activating factor comprising one of more of the factors selected from the group consisting of IL-2, IL-7, IL-10, and CpG; under conditions sufficient to differentiate the transduced B cells into a plasma cell, such that the differentiated transduced B cells express the nucleic acid of interest. In one embodiment of the method, the retroviral vector is a lentiviral vector. In another embodiment of the method, the nucleic acid of interest comprises a nucleic acid encoding at least an immunoglobulin VL and VH region. In a further embodiment of the method, the nucleic acid of interest encodes an antibody protein, or antigen-binding fragment thereof, a fusion protein or a DNA-encoded small molecule. In yet a further embodiment, the antibody is an anti-HIV antibody, an anti-RNA antibody, or an antibody that binds a protein involved in immune regulation. In another embodiment, the CD40L is provided on a cell or a cell line or may be bound to a tissue culture plate or a bead. In certain embodiment of the methods described herein, the promoter is a B cell specific promoter and in particular, is an EEK promoter.

Another aspect provides a method for expressing a nucleic acid of interest in a B cell comprising, transducing a resting B cell with a retroviral vector pseudotyped with measles virus glycoproteins, H and F, wherein said retroviral vector comprises the nucleic acid of interest operably linked to a promoter, under conditions sufficient to transduce at least 20% of the resting B cells; and contacting the transduced resting B cells with a composition comprising CD40L in combination with a B cell activating factor comprising one of more of the factors selected from the group consisting of IL-2, IL-7, IL-10, and CpG; under conditions sufficient to differentiate the transduced B cells into a plasma cell, such that at least 20% of the transduced B cells express the nucleic acid of interest.

In one embodiment, of the methods described herein, the resting B cells are isolated from blood. In a further embodiment of the methods described herein, plasma cells may be characterized by cell surface expression of one or more of the markers selected from the group consisting of, CD38, CD78, Interleukin-6 receptor, CD27high, and CD138.

A further aspect of the disclosure provides a method for transducing and promoting activation of resting B cells, comprising, contacting resting B cells with a retroviral vector pseudotyped with measles virus glycoproteins, H and F, wherein said retroviral vector comprises a nucleic acid of interest operably linked to a promoter, under conditions sufficient to transduce at least 20% of the resting B cells; and contacting the transduced B cells with a composition comprising CD40L in combination with a B cell activating factor such as one of more of the factors selected from the group consisting of IL-2, IL-10, *Staphylococcus aureus* Cowan I (SAC), PMA and CpG; under conditions sufficient to activate the transduced B cells such that at least 20% of the transduced B cells express the nucleic acid of interest. In one embodiment, the retroviral vector is a lentiviral vector. In a further embodiment, the nucleic acid of interest comprises a nucleic acid encoding at least an immunoglobulin $V_L$ and $V_H$ region. In further embodiments, the nucleic acid of interest comprises a nucleic acid encoding interferon-β. In this regard, in other embodiments, the nucleic acid of interest may encode any of a variety of cytokines, such as, but not limited to IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, IL-34, and IL-35, IFN-γ, IFN-α, IFN-β, IFN-ω, C type chemokines XCL1 and XCL2, C—C type chemokines (to date including CCL1-CCL28) and CXC type chemokines (to date including CXCL1-CXCL17), and members of the TNF superfamily (e.g., TNF-α, 4-1 BB ligand, B cell activating factor (BLyS), FAS ligand, Lymphotoxin, OX40L RANKL and TRAIL). In another embodiment, the nucleic acid of interest encodes an antibody protein, or antigen-binding fragment thereof. In yet a further embodiment, the CD40L is provided on a cell or a cell line or may be bound to a tissue culture plate or a bead. In one particular embodiment, the promoter is a B cell specific promoter. In certain embodiments, the B cell is activated and differentiates into a plasma cell that expresses the protein of interest.

These and other aspects of the invention will be evident upon reference to the following detailed description and attached drawings.

DETAILED DESCRIPTION OF THE INVENTION

The present disclosure relates generally to genetically modifying B cells to express a gene of interest and culturing the modified B cells so as to differentiate and activate them to express the protein encoded by the gene of interest. These activated modified B cells are then administered to a subject.

The compositions and methods described herein surprisingly provide the ability to transduce B cells derived from, for example, a simple blood draw, with a nucleic acid of interest and to culture the modified B cells such that they develop into plasma cells (activated B cells) that secrete abundant amounts of the protein encoded by the nucleic acid of interest. One particular advantage of this system is that it only requires about 10 days to produce a protein of interest, unlike systems known in the art which can take as long as 10 weeks. Thus, the present disclosure provides methods that require less time in culture providing commercial and safety advantages as compared to prior methods.

Methods of Culturing and Transducing B Cells

The prototypic example of cells for use with the transduction methods of the disclosure is B cells.

In certain embodiments, the B cells to be used in the methods of this disclosure may be resting B cells, primed or activated B cells, myeloma cells, lymphocytic leukemia B cells, or B lymphoma cells. However, one of ordinary skill in the art will readily appreciate that the vectors and methods of the disclosure may be applied to other cell types. By way of example, cell types that may be modified and activated include any typically nondividing or quiescent cell such as neuroblasts, hematopoietic stem cells and hematopoietic progenitor cells ($CD34^+$ cells), mesenchymal stem cells, mesenchymal progenitor cells, neural and hepatic progenitor and stem cells, dendritic cells, T cells ($CD8^+$ or $CD4^+$ T cells), other leukocyte populations, pluripotent stem cells, multipotent stem cells, etc. Accordingly, certain embodiments of the present disclosure provides populations of cells resulting from this methodology. In certain embodiments, the methods and vectors as described herein may be used to transduce any other cell type desired, such as hepatocytes, epithelial cells, osteoblasts, myocytes, fibroblasts, adipocytes etc.

"Quiescent", as used herein, refers to a cell state wherein the cell is not actively proliferating.

Prior to transduction and differentiation, a source of B cells is obtained from a subject. The term "subject" is intended to include living organisms in which an adaptive immune response can be elicited (e.g., mammals). Examples of subjects include humans, dogs, cats, mice, rats, and transgenic species thereof. B cells can be obtained from a number of sources, including peripheral blood mononuclear cells, bone marrow, lymph node tissue, cord blood, tissue from a site of infection, spleen tissue, and tumors. In certain embodiments of the present disclosure, any number of B cell lines available in the art, may be used. In certain embodiments of the methods described herein, B cells can be obtained from a unit of blood collected from a subject using any number of techniques known to the skilled artisan, such as FICOLL™ (co-polymers of sucrose and epichlorohydrin that may be used to prepare high density solutions) separation. In one preferred embodiment, cells from the circulating blood of an individual are obtained by apheresis or leukapheresis. The apheresis product typically contains lymphocytes, including T cells, monocytes, granulocytes, B cells, other nucleated white blood cells, red blood cells, and platelets. In one embodiment, the cells collected by apheresis may be washed to remove the plasma fraction and to place the cells in an appropriate buffer or media for subsequent processing steps. In one embodiment of the methods described herein, the cells are washed with phosphate buffered saline (PBS). In an alternative embodiment, the wash solution lacks calcium and may lack magnesium or may lack many if not all divalent cations. As those of ordinary skill in the art would readily appreciate a washing step may be accomplished by methods known to those in the art, such as by using a semi-automated "flow-through" centrifuge (for example, the Cobe 2991 cell processor) according to the manufacturer's instructions. After washing, the cells may be resuspended in a variety of biocompatible buffers, such as, for example, PBS. Alternatively, the undesirable components of the apheresis sample may be removed and the cells directly resuspended in culture media.

B cells may be isolated from peripheral blood or leukapheresis using techniques known in the art. For example, PBMCs may be isolated using FICOLL™ (Sigma-Aldrich, St Louis, Mo.) and CD19+ B cells purified by negative or positive selection using any of a variety of antibodies known in the art, such as the Rosette tetrameric complex system (StemCell Technologies, Vancouver, Canada). Other isolation kits are commercially available, such as R&D Systems' MagCellect Human B Cell Isolation Kit (Minneapolis, Minn.).

In certain embodiments, resting B cells may be prepared by sedimentation on discontinuous Percoll gradients, as described in (Defranco et al., (1982) J. Exp. Med. 155:1523). In brief, cells isolated from the 70-75% (density of 1.087-1.097) Percoll interface are typically >95% mIg$^+$, have a uniform, low degree of near forward light scatter and are unresponsive to Con A.

B cells, or other cells of interest, may be transduced with the retroviral vectors described herein using any of a variety of known techniques in the art (see, e.g., Science 12 Apr. 1996 272: 263-267; Blood 2007, 99:2342-2350; Blood 2009, 113: 1422-1431; Blood 2009 Oct. 8; 114(15):3173-80; Blood. 2003; 101(6):2167-2174; Current Protocols in Molecular Biology or Current Protocols in Immunology, John Wiley & Sons, New York, N.Y. (2009)). For example, PBMCs, B- or T-lymphocytes from donors and other B cell cancer cells such as B-CLLs may be isolated and cultured in RPMI 1640 (GibcoBRL Invitrogen, Auckland, New Zealand) or other suitable medium, either serum-free or supplemented with 10% FCS and penicillin/streptomycin and/or other suitable supplements. In certain embodiments, cells are seeded at 1E5 cells in 48-wellplates and concentrated vector added at various doses that may be routinely optimized by the skilled person using routine methodologies. In certain embodiments, B cells may be transferred to MS5 cell monolayer in RPMI supplemented with 10% AB serum, 5% FCS, 50 ng/ml rhSCF, 10 ng/ml rhIL-15 and 5 ng/ml rhIL-2 and medium refreshed periodically as needed. As would be recognized by the skilled person, other suitable media and supplements may be used as desired.

In one embodiment, the B cells are contacted with a retroviral vector as described herein comprising a nucleic acid of interest operably linked to a promoter, under conditions sufficient to transduce at least a portion of the B cells. In one embodiment the B cells are contacted with a retroviral vector as described herein comprising a nucleic acid of interest operably linked to a promoter, under conditions sufficient to transduce at least 20% of the resting B cells. In a further embodiment, the B cells are contacted with a vector as described herein under conditions sufficient to transduce at least 20%, 25%, 30%, 35%, 40%, 45%, 50%, 55%, 60%, 70%, 75%, 80%, 85%, 90%, 95%, 96%, 97%, 98%, 99% or even 100% of the resting B cells. Where activated B cells are transduced, the activated B cells are contacted with a vector as described herein under conditions sufficient to transduce at least 20%, 25%, 30%, 35%, 40%, 45%, 50%, 55%, 60%, 70%, 75%, 80%, 85%, 90%, 95%, 96%, 97%, 98%, 99% or even 100% of the activated B cells.

In certain embodiments, the cells are activated at the time of transduction. In this regard, cells may be prestimulated with Staphylococcus Aureus Cowan (SAC; Calbiochem, San Diego, Calif.); IL-2 for B cells or with anti-hCD3/anti-hCD28/IL-2 for T-cells, at appropriate concentrations known to the skilled person and routinely optimized. Other B cell activating factors (e.g., PMA, as are known to the skilled artisan and described herein may be used.

The present disclosure provides methods of culturing transduced B cells so as to promote differentiation and activation such that the B cells actively produce the transgene-encoded protein. In this regard, the B cells are activated and differentiate into plasma cells. As would be recognized by the skilled person, plasma cells may be identified by cell surface protein expression patterns using standard flow cytometry methods. For example, terminally differentiated plasma cells express relatively few surface antigens, and do not express common pan-B cell markers, such as CD19 and CD20. Instead, plasma cells are identified through flow cytometry by their additional expression of CD38, CD78, the Interleukin-6 receptor and lack of expression of CD45. In humans, CD27 is a good marker for plasma cells, naive B cells are CD27−, memory B-cells are CD27+ and plasma cells are CD27++. CD38 and CD138 are expressed at high levels.

In certain embodiments, it may be desirable to differentiate and activate B cells prior to transduction. Accordingly, any such methods are contemplated herein for use with non-transduced cells.

In one embodiment, the B cells may be contacted with a B cell activating factor, e.g., any of a variety of cytokines, growth factors or cell lines known to activate and/or differentiate B cells (see e.g., Fluckiger, et al. Blood 1998 92: 4509-4520; Luo, et al., Blood 2009 113: 1422-1431). Such factors may be selected from the group consisting of, but not limited to, IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, IL-34, and IL-35, IFN-γ, IFN-α, IFN-β, IFN-ω, C type chemokines XCL1 and XCL2, C—C type chemokines (to date including CCL1-CCL28) and CXC type chemokines (to date including CXCL1-CXCL17), and members of the TNF superfamily (e.g., TNF-α, 4-1BB ligand, B cell activating factor (BLyS), FAS ligand, Lymphotoxin, OX40L RANKL and TRAIL). In particular, transduced B cells (or B cells prior to transduction) may be contacted or cultured on feeder cells. In certain embodiments, the feeder cells are a stromal cell line, e.g., the murine stromal cell lines S17 or MS5. In a further embodiment, purified CD19+ cells may be cultured in the presence of fibroblasts expressing CD40-ligand in the presence of B cell activating factor cytokines such as IL-10 and IL-4. CD40L may also be provided bound to a surface such as tissue culture plate or a bead. In another embodiment, purified CD19+ cells may be cultured in the presence of feeder cells expressing CD40L in presence of one or more cytokines or factors selected from IL-10, IL-4, IL-7, CpG DNA, IL-2, IL-15, IL6, and IFN-α.

In another embodiment, B cell activating factors may be provided by transfection into the B cell or other feeder cell. In this context, one or more factors that promote differentiation of the B cell into an antibody secreting cell and/or one or more factors that promote the longevity of the antibody producing cell may be used. Such factors include, for example, Blimp-1, TRF4, anti-apoptotic factors like Bcl-xl or Bcl5, constitutively active mutants of the CD40 receptor. Further factors which promote the expression of downstream signaling molecules such as TNF receptor-associated factors (TRAFs) may also be used in the activation/differentiation of the B cells. In this regard, cell activation, cell survival, and antiapoptotic functions of the TNF receptor superfamily are mostly mediated by TRAF1-6 (see e.g., R. H. Arch, et al., Genes Dev. 12 (1998), pp. 2821-2830). Downstream effectors of TRAF signaling include transcription factors in the NF-κB and AP-1 family which can turn on genes involved in various aspects of cellular and immune functions. Further, the activation of NF-κB and AP-1 has been shown to provide cells protection from apoptosis via the transcription of antiapoptotic genes.

In an additional embodiment, Epstein Barr virus (EBV)-derived proteins may be useful for the activation/differentiation of B cells or to promote the longevity of the antibody producing cell. EBV-derived proteins include but are not limited to, EBNA-1, EBNA-2, EBNA-3, LMP-1, LMP-2, EBER, miRNAs, EBV-EA, EBV-MA, EBV-VCA and EBV-AN.

Contact of the B cells with B cell activation factors using the methods provided herein leads to, among other things, cell proliferation, modulation of the IgM+ cell surface phenotype to one consistent with an activated mature B cell, secretion of Ig, and isotype switching. CD19+ B cells may be isolated using known and commercially available cell separation kits, such as the MiniMacs cell separation system (Miltenyi Biotech, Bergisch Gladbach, Germany). In certain embodiments, CD40L fibroblasts are irradiated before use in the methods described herein.

In a further embodiment, progenitor cells or B cells may be cultured in the presence of one or more of IL-3, IL-7, Flt3 ligand, thrombopoietin, SCF, IL-2, IL-10, G-CSF and CpG. In certain embodiments, the methods include culturing the B cells or progenitors in the presence of one or more of the aforementioned factors in conjunction with transformed stromal cells (e.g., MS5) providing a low level of anchored CD40L, or CD40L bound to a plate or a bead.

Any of a variety of culture media may be used in the present methods as would be known to the skilled person (see e.g., Current Protocols in Cell Culture, 2000-2009 by John Wiley & Sons, Inc.). In one embodiment, media for use in the methods described herein includes, but is not limited to Iscove modified Dulbecco medium (with or without fetal bovine or other appropriate serum). Illustrative media also includes, but is not limited to, RPMI 1640, AIM-V, DMEM, MEM, α-MEM, F-12, X-Vivo 15, and X-Vivo 20. In further embodiments, the medium may comprise a surfactant, an antibody, plasmanate or a reducing agent (e.g. N-acetyl-cysteine, 2-mercaptoethanol), or one or more antibiotics. In some embodiments, IL-6, soluble CD40L, and a cross-linking enhancer may also used.

B cells or progenitor cells may be cultured under conditions and for sufficient time periods to achieve differentiation and activation desired. In certain embodiments, the B cells or progenitor cells are cultured under conditions and for sufficient time periods such that 10%, 15%, 20%, 25%, 30%, 35%, 40%, 45%, 50%, 55%, 60%, 65%, 70%, 75%, 80%, 85%, 90%, 95%, or even 100% of the B cells are differentiated and/or activated as desired. In one embodiment, the B cells are activated and differentiate into plasma cells. As would be recognized by the skilled person, plasma cells may be identified by cell surface protein expression patterns using standard flow cytometry methods as described elsewhere herein, such as by expression of CD38, CD78, the Interleukin-6 receptor, $CD27^{high}$ CD138, and lack of expression of common pan-B cell markers, such as CD19 and CD20 and lack of expression of CD45.

In certain embodiments, cells are cultured for 1-7 days. In further embodiments, cells are cultured 7, 14, 21 days or longer. Thus, cells may be cultured under appropriate conditions for 1, 2, 3, 4, 5, 6, 7, 8, 9, 10, 11, 12, 13, 14, 15, 16, 17, 18, 19, 20, 21, 22, 23, 24, 25, 26, 27, 28, 29, or more days. Cells are replated, media and supplements may be added or changed as needed using techniques known in the art.

In certain embodiments, the transduced B cells or progenitor cells may be cultured under conditions and for sufficient time periods such that at least 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99% or 100% of the cells are differentiated and activated to produce Ig and/or to express the transgene of interest.

The induction of B cell activation may be measured by techniques such as $^3$H-uridine incorporation into RNA (as B cells differentiate, RNA synthesis increases), or by $^3$H-thymidine incorporation, which measures DNA synthesis associated with cell proliferation. For optimal measurement of B cell proliferation, interleukin-4 (IL-4) may be added to the culture medium at an appropriate concentration, such as about 10 ng/ml.

Alternatively, B cell activation may be measured as a function of immunoglobulin secretion. For example, CD40L may be added to resting B cells together with IL-4 (e.g., 10 ng/ml) and IL-5 (e.g., 5 ng/ml) or other cytokines suited to activation of B cells. Flow cytometry may also be used for measuring cell surface markers typical of activated B cells. See e.g., Civin C I, Loken M R, Int'l J. Cell Cloning 1987; 5:1-16; Loken, M R, et al., Flow Cytometry Characterization of Erythroid, Lymphoid and Monomyeloid Lineages in Normal Human Bone Marrow, in Flow Cytometry in Hematology, Laerum O D, Bjerksnes R. eds., Academic Press, New York 1992; pp. 31-42; and LeBein T W, et al., Leukemia 1990; 4:354-358.

After culture for an appropriate period of time, such as from 2, 3, 4, 5, 6, 7, 8, 9, or more days, generally around 3 days, an additional volume of culture medium may be added. Supernatant from individual cultures may be harvested at various times during culture and quantitated for IgM and $IG_1$ as described in Noelle et al., (1991) J. Immunol. 146:1118-1124. In further embodiments, the cultures may be harvested and measured for expression of the transgene of interest using flow cytometry, ELISA, ELISPOT or other assay known in the art.

In further embodiments, enzyme-linked immunoabsorbtion assay (ELISA) may be used for measuring IgM or other antibody isotype production or for production of the transgene of interest. In certain embodiments, IgG determinations may be made using commercially available antibodies such as goat antihuman IgG, as capture antibody, followed by detection using any of a variety of appropriate detection reagents such as biotinylated goat antihuman Ig, streptavidin alkaline phosphatase and substrate.

Viral Vectors

Certain embodiments employ viral vectors to transduce plasma cells such as B cells with the expression systems described herein. Examples of viral vectors include, without limitation, adenovirus-based vectors, adeno-associated virus (AAV)-based vectors, retroviral vectors, retroviral-adenoviral vectors, and vectors derived from herpes simplex viruses (HSVs), including amplicon vectors, replication-defective HSV and attenuated HSV (see, e.g., Krisky, Gene Ther. 5: 1517-30, 1998; Pfeifer, Annu. Rev. Genomics Hum. Genet. 2:177-211, 2001, each of which is incorporated by reference in its entirety).

Certain embodiments relate to the use of retroviral vectors, or vectors derived from retroviruses. "Retroviruses" are enveloped RNA viruses that are capable of infecting animal cells, and that utilize the enzyme reverse transcriptase in the early stages of infection to generate a DNA copy from their RNA genome, which is then typically integrated into the host genome. Examples of retroviral vectors Moloney murine leukemia virus (MLV)-derived vectors, retroviral vectors based on a Murine Stem Cell Virus, which provides long-term stable expression in target cells such as hematopoietic precursor cells and their differentiated progeny (see, e.g., Hawley et al., PNAS USA 93:10297-10302, 1996; Keller et al., Blood 92:877-887, 1998), hybrid vectors (see, e.g., Choi, et al., Stem Cells 19:236-246, 2001), and complex retrovirus-derived vectors, such as lentiviral vectors.

As noted above, certain embodiments employ lentiviral vectors. The term "lentivirus" refers to a genus of complex retroviruses that are capable of infecting both dividing and non-dividing cells. Examples of lentiviruses include HIV (human immunodeficiency virus; including HIV type 1, and HIV type 2), visna-maedi, the caprine arthritis-encephalitis virus, equine infectious anemia virus, feline immunodeficiency virus (FIV), bovine immune deficiency virus (BIV), and simian immunodeficiency virus (SIV). Lentiviral vectors can be derived from any one or more of these lentiviruses (see, e.g., Evans et al., *Hum Gene Ther.* 10:1479-1489, 1999; Case et al., *PNAS USA* 96:2988-2993, 1999; Uchida et al., *PNAS USA* 95:11939-11944, 1998; Miyoshi et al., *Science* 283:682-686, 1999; Sutton et al., *J Virol* 72:5781-5788, 1998; and Frecha et al., *Blood.* 112:4843-52, 2008, each of which is incorporated by reference in its entirety).

It has been documented that resting T and B cells can be transduced by a VSVG-coated LV carrying most of the HIV accessory proteins (vif, vpr, vpu, and nef) (see e.g., Frecha et al., 2010 *Mol. Therapy* 18:1748). However, including such accessory proteins raises safety concerns. One advantage of the vectors described herein is that there is no need for the accessory proteins. Therefore, in certain embodiments the retroviral vector comprises certain minimal sequences from a lentivirus genome, such as the HIV genome or the SIV genome. The genome of a lentivirus is typically organized into a 5' long terminal repeat (LTR) region, the gag gene, the pol gene, the env gene, the accessory genes (e.g., nef, vif, vpr, vpu, tat, rev) and a 3' LTR region. The viral LTR is divided into three regions referred to as U3, R (repeat) and U5. The U3 region contains the enhancer and promoter elements, the U5 region contains the polyadenylation signals, and the R region separates the U3 and U5 regions. The transcribed sequences of the R region appear at both the 5' and 3' ends of the viral RNA (see, e.g., "RNA Viruses: A Practical Approach" (Alan J. Cann, Ed., Oxford University Press, 2000); O Narayan, *J. Gen. Virology.* 70:1617-1639, 1989; Fields et al., Fundamental Virology Raven Press., 1990; Miyoshi et al., *J Virol.* 72:8150-7, 1998; and U.S. Pat. No. 6,013,516, each of which is incorporated by reference in its entirety). Lentiviral vectors may comprise any one or more of these elements of the lentiviral genome, to regulate the activity of the vector as desired, or, they may contain deletions, insertions, substitutions, or mutations in one or more of these elements, such as to reduce the pathological effects of lentiviral replication, or to limit the lentiviral vector to a single round of infection.

Typically, a minimal retroviral vector comprises certain 5'LTR and 3'LTR sequences, one or more genes of interest (to be expressed in the target cell), one or more promoters, and a cis-acting sequence for packaging of the RNA. Other regulatory sequences can be included, as described herein and known in the art. The viral vector is typically cloned into a plasmid that may be transfected into a packaging cell line, such as a eukaryotic cell (e.g., 293-HEK), and also typically comprises sequences useful for replication of the plasmid in bacteria.

In certain embodiments, the viral vector comprises sequences from the 5' and/or the 3' LTRs of a retrovirus such as a lentivirus. The LTR sequences may be LTR sequences from any lentivirus from any species. For example, they may be LTR sequences from HIV, SIV, FIV or BIV. Preferably the LTR sequences are HIV LTR sequences.

In certain embodiments, the viral vector comprises the R and U5 sequences from the 5' LTR of a lentivirus and an inactivated or "self-inactivating" 3' LTR from a lentivirus. A "self-inactivating 3' LTR" is a 3' long terminal repeat (LTR) that contains a mutation, substitution or deletion that prevents the LTR sequences from driving expression of a downstream gene. A copy of the U3 region from the 3' LTR acts as a template for the generation of both LTR's in the integrated provirus. Thus, when the 3' LTR with an inactivating deletion or mutation integrates as the 5' LTR of the provirus, no transcription from the 5' LTR is possible. This eliminates competition between the viral enhancer/promoter and any internal enhancer/promoter. Self-inactivating 3' LTRs are described, for example, in Zufferey et al., *J Virol.* 72:9873-9880, 1998; Miyoshi et al., *J Virol.* 72:8150-8157, 1998; and Iwakuma et al., *Virology* 261:120-132, 1999, each of which is incorporated by reference in its entirety. Self-inactivating 3' LTRs may be generated by any method known in the art. In certain embodiments, the U3 element of the 3' LTR contains a deletion of its enhancer sequence, preferably the TATA box, Spl and/or NF-kappa B sites. As a result of the self-inactivating 3' LTR, the provirus that is integrated into the host cell genome will comprise an inactivated 5' LTR.

The viral vectors provided herein typically comprises a gene that encodes a protein (or other molecule, such as siRNA) that is desirably expressed in one or more target cells. Preferably the gene of interest is located between the 5' LTR and 3' LTR sequences. Further, the gene of interest is preferably in a functional relationship with other genetic elements, for example, transcription regulatory sequences such as promoters and/or enhancers, to regulate expression of the gene of interest in a particular manner once the gene is incorporated into the target cell. In certain embodiments, the useful transcriptional regulatory sequences are those that are highly regulated with respect to activity, both temporally and spatially.

In certain embodiments, one or more additional genes may be incorporated as a safety measure, mainly to allow for the selective killing of infected target cells within a heterogeneous population, such as within a human patient. In one exemplary embodiment, the selected gene is a thymidine kinase gene (TK), the expression of which renders a target cell susceptible to the action of the drug gancyclovir. In a further embodiment, the suicide gene is a caspase 9 suicide gene.

In certain embodiments, a gene encoding a marker protein may be placed before or after the primary gene to allow for identification of cells that are expressing the desired protein. Certain embodiments incorporate a fluorescent marker protein, such as green fluorescent protein (GFP) or red fluorescent protein (RFP), along with the primary gene of interest. If one or more additional reporter genes are included, IRES sequences or 2A elements may also be included, separating the primary gene of interest from a reporter gene and/or any other gene of interest.

Certain embodiments may employ genes that encode one or more selectable markers. Examples include selectable markers that are effective in a eukaryotic cell or a prokaryotic cell, such as a gene for a drug resistance that encodes a factor necessary for the survival or growth of transformed host cells grown in a selective culture medium. Exemplary selection genes encode proteins that confer resistance to antibiotics or other toxins, e.g., G418, hygromycin B, puromycin, zeocin, ouabain, blasticidin, ampicillin, neomycin, methotrexate, or tetracycline, complement auxotrophic deficiencies, or supply may be present on a separate plasmid and introduced by co-transfection with the viral vector.

Certain viral vectors such as retroviral vectors employ one or more heterologous promoters, enhancers, or both. In certain embodiments, the U3 sequence from a retroviral or lentiviral 5' LTR may be replaced with a promoter or enhancer sequence in the viral construct. Certain embodiments employ an "internal" promoter/enhancer that is located between the 5' LTR and 3' LTR sequences of the viral vector, and is operably linked to the gene of interest. A "functional relationship" and "operably linked" mean, without limitation, that the gene is in the correct location and orientation with respect to the promoter and/or enhancer, such that expression of the gene will be affected when the promoter and/or enhancer is contacted with the appropriate regulatory molecules. Any enhancer/promoter combination may be used that either regulates (e.g., increases, decreases) expression of the viral RNA genome in the packaging cell line, regulates expression of the selected gene of interest in an infected target cell, or both.

A promoter is an expression control element formed by a DNA sequence that permits binding of RNA polymerase and transcription to occur. Promoters are untranslated sequences that are located upstream (5') of the start codon of a selected gene of interest (typically within about 100 to 1000 bp) and control the transcription and translation of the coding polynucleotide sequence to which they are operably linked. Promoters may be inducible or constitutive. Inducible promoters initiate increased levels of transcription from DNA under their control in response to some change in culture conditions, such as a change in temperature.

A variety of promoters are known in the art, as are methods for operably linking the promoter to the polynucleotide coding sequence. Both native promoter sequences and many heterologous promoters may be used to direct expression of the selected gene of interest. Certain embodiments employ heterologous promoters, because they generally permit greater transcription and higher yields of the desired protein as compared to the native promoter.

Certain embodiments may employ heterologous viral promoters. Examples of such promoters include those obtained from the genomes of viruses such as polyoma virus, fowlpox virus, adenovirus, bovine papilloma virus, avian sarcoma virus, cytomegalovirus, a retrovirus, hepatitis-B virus and Simian Virus 40 (SV40). Certain embodiments may employ heterologous mammalian promoter, such as the actin promoter, an immunoglobulin promoter, a heat-shock promoter, or a promoter that is associated with the native sequence of the gene of interest. Typically, the promoter is compatible with the target cell, such as a quiescent B-lymphocyte, an activated B-lymphocyte, a plasma B cell, a memory B cell or other lymphocyte target cell.

Certain embodiments may employ the one or more of the RNA polymerase II and III promoters. A suitable selection of RNA polymerase III promoters can be found, for example, in Paule and White. *Nucleic Acids Research.*, Vol. 28, pp 1283-1298, 2000, which is incorporated by reference in its entirety. RNA polymerase II and III promoters also include any synthetic or engineered DNA fragments that can direct RNA polymerase II or III, respectively, to transcribe its downstream RNA coding sequences. Further, the RNA polymerase II or III (Pol II or III) promoter or promoters used as part of the viral vector can be inducible. Any suitable inducible Pol II or III promoter can be used with the methods described herein. Exemplary Pol II or III promoters include the tetracycline responsive promoters provided in Ohkawa and Taira, *Human Gene Therapy*, Vol. 11, pp 577-585, 2000; and Meissner et al., *Nucleic Acids Research*, Vol. 29, pp 1672-1682, 2001, each of which is incorporated by reference in its entirety.

Non-limiting examples of constitutive promoters that may be used include the promoter for ubiquitin, the CMV promoter (see, e.g., Karasuyama et al., *J. Exp. Med.* 169:13, 1989), the β-actin (see, e.g., Gunning et al., *PNAS USA* 84:4831-4835, 1987), and the pgk promoter (see, e.g., Adra et al., *Gene* 60:65-74, 1987); Singer-Sam et al., *Gene* 32:409-417, 1984; and Dobson et al., *Nucleic Acids Res.* 10:2635-2637, 1982, each of which is incorporated by reference). Non-limiting examples of tissue specific promoters include the Ick promoter (see, e.g., Garvin et al., *Mol. Cell Biol.* 8:3058-3064, 1988; and Takadera et al., *Mol. Cell Biol.* 9:2173-2180, 1989), the myogenin promoter (Yee et al., *Genes and Development* 7:1277-1289. 1993), and the thy1 (see, e.g., Gundersen et al., *Gene* 113:207-214, 1992).

Additional examples of promoters include the ubiquitin-C promoter, the human μ heavy chain promoter or the Ig heavy chain promoter (e.g., MH-b12), and the human κ light chain promoter or the Ig light chain promoter (e.g., EEK-b12), which are functional in B-lymphocytes. The MH-b12 promoter contains the human μ heavy chain promoter preceded by the iEμ enhancer flanked by matrix association regions, and the EEK-b12 promoter contains the κ light chain promoter preceded an intronic enhancer (iEκ), a matrix associated region, and a 3' enhancer (3'Eκ) (see, e.g., Luo et al., *Blood.* 113:1422-1431, 2009, and published U.S. patent application 20100203630). Accordingly, certain embodiments may employ one or more of these promoter or enhancer elements.

As noted above, certain embodiments may employ enhancer elements, such as an internal enhancer, to increase expression of the gene of interest. Enhancers are cis-acting elements of DNA, usually about 10 to 300 bp in length, that act on a promoter to increase its transcription. Certain enhancer sequences may be derived from mammalian genes (e.g., globin, elastase, albumin, α-fetoprotein, insulin), such as the iEμ enhancer, the iEκ intronic enhancer, and the 3' Eκ enhancer. Also included are enhancers from a eukaryotic virus, including the SV40 enhancer on the late side of the replication origin (bp 100-270), the cytomegalovirus early promoter enhancer, the polyoma enhancer on the late side of the replication origin, and adenovirus enhancers. Enhancers may be spliced into the vector at a position 5' or 3' to the antigen-specific polynucleotide sequence, but are preferably located at a site 5' from the promoter. Persons of skill in the art will select the appropriate enhancer based on the desired expression pattern.

In certain embodiments, promoters may be selected to allow for inducible expression of the gene. A number of systems for inducible expression are known in the art, including the tetracycline responsive system and the lac operator-repressor system. It is also contemplated that a combination of promoters may be used to obtain the desired expression of the gene of interest. The skilled artisan will be able to select a promoter based on the desired expression pattern of the gene in the organism and/or the target cell of interest.

Certain viral vectors contain cis-acting packaging sequences to promote incorporation of the genomic viral RNA into the viral particle. Examples include psi-sequences. Such cis-acting sequences are known in the art.

In certain embodiments, the viral vectors described herein may express two or more genes, which may be accomplished, for example, by incorporating an internal promoter that is operably linked to each separate gene beyond the first gene, by incorporating an element that facilitates co-expression such as an internal ribosomal entry sequence (IRES) element (U.S. Pat. No. 4,937,190, incorporated by reference) or a 2A element, or both.

Merely by way of illustration, IRES or 2A elements may be used when a single vector comprises sequences encoding each chain of an immunoglobulin molecule with a desired specificity. For instance, the first coding region (encoding either the heavy or light chain) may be located immediately downstream from the promoter, and the second coding region (encoding the other chain) may be located downstream from the first coding region, with an IRES or 2A element located between the first and second coding regions, preferably immediately preceding the second coding region. In other embodiments, an IRES or 2A element is used to co-express an unrelated gene, such as a reporter gene, a selectable marker, or a gene that enhances immune function.

Examples of IRES sequences that can be used include, without limitation, the IRES elements of encephalomyelitis virus (EMCV), foot-and-mouth disease virus (FMDV), Theiler's murine encephalomyelitis virus (TMEV), human rhinovirus (HRV), coxsackievirus (CSV), poliovirus (POLIO), Hepatitis A virus (HAV), Hepatitis C virus (HCV), and Pestiviruses (e.g., hog cholera virus (HOCV) and bovine viral diarrhea virus (BVDV)) (see, e.g., Le et al., *Virus Genes* 12:135-147, 1996; and Le et al., *Nuc. Acids Res.* 25:362-369, 1997, each of which is incorporated by reference in their entirety). One example of a 2A element includes the F2A sequence from foot-and-mouth disease virus.

In certain embodiments, the viral vectors provided herein may also contain additional genetic elements to achieve a desired result. For example, certain viral vectors may include a signal that facilitates nuclear entry of the viral genome in the target cell, such as an HIV-1 flap signal. As a further example, certain viral vectors may include elements that facilitate the characterization of the provirus integration site in the target cell, such as a tRNA amber suppressor sequence. Certain viral vectors may contain one or more genetic elements designed to enhance expression of the gene of interest. For example, a woodchuck hepatitis virus responsive element (WRE) may be placed into the construct (see, e.g., Zufferey et al., *J. Virol.* 74:3668-3681, 1999; and Deglon et al., *Hum. Gene Ther.* 11:179-190, 2000, each of which is incorporated by reference in its entirety). As another example, a chicken β-globin insulator may also be included in the viral construct. This element has been shown to reduce the chance of silencing the integrated provirus in the target cell due to methylation and heterochromatinization effects. In addition, the insulator may shield the internal enhancer, promoter and exogenous gene from positive or negative positional effects from surrounding DNA at the integration site on the chromosome. Certain embodiments employ each of these genetic elements.

In certain embodiments, the viral vectors (e.g., retroviral, lentiviral) provided herein are "pseudo-typed" with one or more selected viral glycoproteins or envelope proteins, mainly to target selected cell types. Pseudo-typing refers to generally to the incorporation of one or more heterologous viral glycoproteins onto the cell-surface virus particle, often allowing the virus particle to infect a selected cell that differs from its normal target cells. A "heterologous" element is derived from a virus other than the virus from which the RNA genome of the viral vector is derived. Typically, the glycoprotein-coding regions of the viral vector have been genetically altered such as by deletion to prevent expression of its own glycoprotein. Merely by way of illustration, the envelope glycoproteins gp41 and/or gp120 from an HIV-derived lentiviral vector are typically deleted prior to pseudo-typing with a heterologous viral glycoprotein.

In certain embodiments, the viral vector is pseudo-typed with a heterologous viral glycoprotein that targets plasma cells such as B-lymphocytes. In certain embodiments, the viral glycoprotein allows selective infection or transduction of resting or quiescent B-lymphocytes. In certain embodiments, the viral glycoprotein allows selective infection of activated B-lymphocytes. In certain embodiments, the viral glycoprotein allows infection or transduction of both quiescent B-lymphocytes and activated B-lymphocytes. In certain embodiments, viral glycoprotein allows infection of B cell chronic lymphocyte leukemia cells. In certain embodiments, the heterologous viral glycoprotein is derived from the glycoprotein of the measles virus, such as the Edmonton measles virus. Certain embodiments pseudo-type the measles virus glycoproteins hemagglutinin (H), fusion protein (F), or both (see, e.g., Frecha et al., *Blood.* 112:4843-52, 2008; and Frecha et al., *Blood.* 114:3173-80, 2009, each of which is incorporated by reference in its entirety). In further embodiments, the viral vector comprises an embedded antibody binding domain, such as one or more variable regions (e.g., heavy and light chain variable regions) which serves to target the vector to a particular cell type.

Generation of viral vectors can be accomplished using any suitable genetic engineering techniques known in the art, including, without limitation, the standard techniques of restriction endonuclease digestion, ligation, transformation, plasmid purification, PCR amplification, and DNA sequencing, for example as described in Sambrook et al. (Molecular Cloning: A Laboratory Manual. Cold Spring Harbor Laboratory Press, N.Y. (1989)), Coffin et al. (Retroviruses. Cold Spring Harbor Laboratory Press, N.Y. (1997)) and "RNA Viruses: A Practical Approach" (Alan J. Cann, Ed., Oxford University Press, (2000)).

Any variety of methods known in the art may be used to produce suitable retroviral particles whose genome comprises an RNA copy of the viral vector. As one method, the viral vector may be introduced into a packaging cell line that packages the viral genomic RNA based on the viral vector into viral particles with a desired target cell specificity. The packaging cell line typically provides in trans the viral proteins that are required for packaging the viral genomic RNA into viral particles and infecting the target cell, including the structural gag proteins, the enzymatic pal proteins, and the envelope glycoproteins.

In certain embodiments, the packaging cell line may stably express certain of the necessary or desired viral proteins (e.g., gag, pol) (see, e.g., U.S. Pat. No. 6,218,181, herein incorporated by reference). In certain embodiments, the packaging cell line may be transiently transfected with plasmids that encode certain of the necessary or desired viral proteins (e.g., gag, pol, glycoprotein), including the measles virus glycoprotein sequences described herein. In one exemplary embodiment, the packaging cell line stably expresses the gag and pol sequences, and the cell line is then transfected with a plasmid encoding the viral vector and a plasmid encoding the glycoprotein. Following introduction of the desired plasmids, viral particles are collected and processed accordingly, such as by ultracentrifugation to achieve a concentrated stock of viral particles. Exemplary packaging cell lines include 293 (ATCC CCL X), HeLa (ATCC CCL 2), D17 (ATCC CCL 183), MDCK (ATCC CCL 34), BHK (ATCC CCL-10) and Cf2Th (ATCC CRL 1430) cell lines.

Gene/Nucleic Acid of Interest

As used herein "gene of interest" or "gene" or "nucleic acid of interest" refers to a nucleic acid of interest encoding a protein of interest to be expressed in the target transduced cell. While the term "gene" may be used, this is not to imply that this is a gene as found in genomic DNA and is used interchangeably with the term "nucleic acid". Generally, the nucleic acid of interest provides suitable nucleic acid for encoding the protein of interest and may comprise cDNA or DNA and may or may not include introns but generally does not include introns. As noted elsewhere, the nucleic acid of interest is operably linked to expression control sequences to effectively express the protein of interest in the target cell. In certain embodiments, the vectors described herein may comprise two or more genes of interest, and may include 2, 3, or 4 genes of interest, such as for example, the heavy and light chains of an immunoglobulin that may be organized using an internal promoter as described herein.

The recitation "polynucleotide" or "nucleic acid" as used herein designates mRNA, RNA, cRNA, cDNA or DNA. The term typically refers to polymeric form of nucleotides of at least 10 bases in length, either ribonucleotides or deoxynucleotides or a modified form of either type of nucleotide. The term includes single and double stranded forms of DNA and RNA.

The nucleic acid or gene of interest may be any nucleic acid encoding a protein of interest. A protein of interest for use as described herein comprises any protein providing an activity desired. In this regard, a protein of interest includes, but is not limited to, an antibody or antigen-binding fragment thereof, a cell surface receptor, a secreted protein such as a cytokine (lymphokines, interleukins, interferons, or chemokines), a DNA-encoded small molecule (see e.g., *Nature Chemical Biology* 5, 647-654 (2009)), or an adhesion molecule.

In one embodiment, the nucleic acid encodes an antibody or antigen-binding fragment thereof. Exemplary antigen binding fragments include domain antibodies, sFv, scFv, Fab, Fab', F(ab')2, Fv). In one embodiment, the antibody encoded by the nucleic acid comprises at least the antigen binding domain of the HIV neutralizing antibody, b12 (see, e.g., *J Virol* 2003, 77:5863-5876; *J Virol*. 1994 August; 68(8):4821-8; *Proc Natl Acad Sci USA*. 1992, 89:9339-9343; exemplary sequences are provided in GenBank Accession Nos. for the b12 light chain (AAB26306.1 GI 299737) and heavy chain (AAB26315.1 GI 299746)). In a further embodiment, the antibody encoded by the nucleic acid of interest comprises Fuzeon™ (T-20/enfuvirtide/pentafuside/DP-178). DP-178 is an amino acid sequence from gp41 on HIV and interferes with HIV's ability to fuse with its target cell. Fuzeon may be produced synthetically using methods known to the skilled person (see e.g., 2001 *J. Virol*. 75:3038-3042; It should be noted that it is highly unlikely that the methods described in this paper resulted in secretion of a therapeutic dose of the DP-178 peptide).

In one particular embodiment, the nucleic acid of interest encodes an immunologically active protein. In certain embodiments, a nucleic acid of interest encodes a protein, or a biologically active fragment thereof, that induces an immune vaccine-like reaction through the presentation of the protein on the surface of a B cell, T cell or other immune cell. In certain embodiments, the protein of interest influences the regulation of B cells, for example but not limited to promoting cell division, promoting differentiation into different B lineages, inactivating or killing cells, or regulates production or activity of other introduced DNA elements. Interleukins are known to the skilled person and to date include IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, IL-22, IL-23, IL-24, IL-25, IL-26, IL-27, secreted form of the p28 subunit of IL27, IL-28, IL-29, IL-30, IL-31, IL-32, IL-33, IL-34, and IL-35. Interferons include IFN-γ, IFN-α, IFN-β and IFN-ω. The chemokines contemplated for use herein include the C type chemokines XCL1 and XCL2, C—C type chemokines (to date including CCL1-CCL28) and CXC type chemokines (to date including CXCL1-CXCL17). Also contemplated as a gene of interest are members of the TNF superfamily (e.g., TNF-α, 4-1 BB ligand, B cell activating factor, FAS ligand, Lymphotoxin, OX40L RANKL, and TRAIL).

In certain embodiments, the protein of interest induces immunological tolerance. In this regard, the protein of interest may comprise an IgG-antigen fusion protein (see e.g., *Cellular Immunology* 235(1), 2005, 12-20).

In a further embodiment, the gene(s) of interest encodes one or more factors that promote differentiation of the B cell into an antibody secreting cell and/or one or more factors that promote the longevity of the antibody producing cell. Such factors include, for example, Blimp-1, TRF4, anti-apoptotic factors like Bcl-xl or Bcl5, constitutively active mutants of the CD40 receptor. Further genes of interest encode factors which promote the expression of downstream signaling molecules such as TNF receptor-associated factors (TRAFs). In this regard, cell activation, cell survival, and antiapoptotic functions of the TNF receptor superfamily are mostly mediated by TRAF1-6 (see e.g., R. H. Arch, et al., *Genes Dev.* 12 (1998), pp. 2821-2830). Downstream effectors of TRAF signaling include transcription factors in the NF-κB and AP-1 family which can turn on genes involved in various aspects of cellular and immune functions. Further, the activation of NF-κB and AP-1 has been shown to provide cells protection from apoptosis via the transcription of antiapoptotic genes.

In an additional embodiment, the nucleic acid(s) of interest encodes one or more Epstein Barr virus (EBV)-derived proteins. EBV-derived proteins include but are not limited to, EBNA-1, EBNA-2, EBNA-3, LMP-1, LMP-2, EBER, EBV-EA, EBV-MA, EBV-VCA and EBV-AN.

In one particular embodiment, the nucleic acid of interest encodes an antibody or an antigen-binding fragment thereof. In this regard, the antibody may be a natural antibody or a custom, recombinantly engineered antibody. Fusion proteins comprising an antibody or portion thereof are specifically contemplated to be encoded by the vectors described herein.

In one embodiment, an antibody or fragment thereof according to the present disclosure has an amino acid sequence of an anti-HIV antibody, such as the m36 anti-HIV antibody (see e.g., *Proc Natl Acad Sci USA*. 2008 Nov. 4; 105(44):17121-6), or an amino acid molecule having at least 60%, 80%, 85%, 90%, 95%, 96%, 97%, 98% or 99% sequence identity with an amino acid sequence of an anti-HIV antibody, such as m36. In particular, fusion proteins comprising m36, or derivatives thereof, are specifically contemplated, such as m36L2CD4Fc (see e.g., *Antiviral Research* volume 88, Issue 1, October 2010, Pages 107-115).

In a further embodiment, the antibody encoded by the transgene of the disclosure binds to an autoantigen. In certain embodiments, the autoantigen in this regard is associated with the development of multiple sclerosis or Type 1 diabetes, including but not limited to MBP, alphaB-crystallin, S100beta, proteolipid protein (PLP), HSP105, epithelial isoform of bullous pemphigoid (BP) antigen 1 (BPAG1-e), lipids, and myelin oligodendrocyte glycoprotein (MOG)-alpha and MOG-beta isoforms or any of a variety of islet cell autoantigens (e.g., sialoglycolipid, glutamate decarboxylase, insulin, insulin receptor, 38 kD, bovine serum albumin, glucose transporter, hsp 65, carboxypeptidase H, 52 kD, ICA 12/ICA512, 150 kD, and RIN polar). Antibodies to these autoantigens are known in the art and may be sequenced and made recombinantly using routine techniques (see e.g., *J. Clin. Invest.* 107(5): 555-564 (2001)).

In a further embodiment, the antibody binds to a cancer-associated antigen. Cancer-associated antigens may be derived from a variety of tumor proteins. Illustrative tumor proteins useful in the present disclosure include, but are not limited to any one or more of, p53, MAGE-A1, MAGE-A2, MAGE-A3, MAGE-A4, MAGE-A6, MAGE-A10, MAGE-A12, BAGE, DAM-6, -10, GAGE-1, -2, -8, GAGE-3, -4, -5, -6, -7B, NA88-A, NY-ESO-1, MART-1, MC1R, Gp100, PSA, PSM, Tyrosinase, TRP-1, TRP-2, ART-4, CAMEL, CEA, Cyp-B, Her2/neu (e.g., the antibody may be derived from the Her2-specific mAb, Herceptin®), hTERT, hTRT, iCE, MUC1, MUC2, PRAME, P15, RU1, RU2, SART-1, SART-3, WT1, AFP, β-catenin/m, Caspase-8/m, CEA, CDK-4/m, ELF2M, GnT-V, G250, HSP70-2M, HST-2, KIAA0205, MUM-1, MUM-2, MUM-3, Myosin/m, RAGE, SART-2, TRP-2/INT2, 707-AP, Annexin II, CDC27/m, TPI/mbcr-abl, ETV6/AML, LDLR/FUT, Pml/RARα, and TEL/AML1. These and other tumor proteins are known to the skilled artisan.

In further embodiments, the nucleic acid of interest encodes a peptide or other binding domain with a particular functional attribute, such as, but not limited to, an inhibitory activity, ability to induce cell death in cancer cells, or ability to slow or inhibit cancer cell proliferation. In this regard, in one embodiment, a peptide or binding domain encoded by the nucleic acid of interest may bind any of the target proteins described herein, such as a cancer-associated antigen as described above, CD4, HIV gp120 or other viral protein, ICAM-3, DC-SIGN (see e.g., U.S. Pat. No. 7,301,010). In certain embodiments, the peptides may be derived from pathogenic and nonpathogenic bacteria and green plants. Illustrative peptides are disclosed in U.S. Pat. Nos. 7,084,105, 7,301,010, 7,338,766, 7,381,701, 7,491,394, 7,511,117, 7,556,810. In one embodiment, the nucleic acid of interest encodes azurin-p28 (NSC745104) a peptide inhibitor of p53 ubiquitination (see e.g., *Cancer Chemother Pharmacol* 2010, DOI 10.1007/s00280-010-1518-3; U.S. Pat. No. 7,084,105). In a further embodiment, the nucleic acid of interest encodes a factor known as Ghrelin, which induces appetite and can be used to treat cancer patients (see e.g., *Obes Facts.* 2010 3:285-92; *FASEB J.* 18 (3): 439-56). In another embodiment, the nucleic acid of interest encodes a binding peptide that binds to and inhibits angiopoietin 1 and 2 (see, e.g., AMG386, an Fc fragment of an antibody (peptibody) used to treat cancer;

In certain embodiments, tumor antigens may be identified directly from an individual with cancer. In this regard, screens can be carried out using a variety of known technologies. For example, in one embodiment, a tumor biopsy is taken from a patient, RNA is isolated from the tumor cells and screened using a gene chip (for example, from Affymetrix, Santa Clara, Calif.) and a tumor antigen is identified. Once the tumor target antigen is identified, it may then be cloned, expressed and purified using techniques known in the art.

An "antibody", as used herein, includes both polyclonal and monoclonal antibodies; primatized (e.g., humanized); murine; mouse-human; mouse-primate; and chimeric; and may be an intact molecule, a fragment thereof (such as scFv, Fv, Fd, Fab, Fab' and F(ab)'$_2$ fragments), or multimers or aggregates of intact molecules and/or fragments; and may occur in nature or be produced, e.g., by immunization, synthesis or genetic engineering; an "antibody fragment," as used herein, refers to fragments, derived from or related to an antibody, which bind antigen and which in some embodiments may be derivatized to exhibit structural features that facilitate clearance and uptake, e.g., by the incorporation of galactose residues. This includes, e.g., F(ab), F(ab)'$_2$, scFv, light chain variable region ($V_L$), heavy chain variable region ($V_H$), and combinations thereof.

Sources include antibody gene sequences from various species (which can be formatted as antibodies, sFvs, scFvs or Fabs, such as in a phage library), including human, camelid (from camels, dromedaries, or llamas; Hamers-Casterman et al. (1993) *Nature*, 363:446 and Nguyen et al. (1998) *J. Mol. Biol.*, 275:413), shark (Roux et al. (1998) *Proc. Nat'l. Acad. Sci. (USA)* 95:11804), fish (Nguyen et al. (2002) *Immunogenetics*, 54:39), rodent, avian, ovine, sequences that encode random peptide libraries or sequences that encode an engineered diversity of amino acids in loop regions of alternative non-antibody scaffolds, such as fibrinogen domains (see, e.g., Weisel et al. (1985) *Science* 230:1388), Kunitz domains (see, e.g., U.S. Pat. No. 6,423,498), lipocalin domains (see, e.g., WO 2006/095164), V-like domains (see, e.g., US Patent Application Publication No. 2007/0065431), C-type lectin domains (Zelensky and Gready (2005) *FEBS J.* 272:6179), mAb$^2$ or Fcab™ (see, e.g., PCT Patent Application Publication Nos. WO 2007/098934; WO 2006/072620), or the like.

Terms understood by those in the art as referring to antibody technology are each given the meaning acquired in the art, unless expressly defined herein. For example, the terms "$V_L$" and "$V_H$" refer to the variable binding region derived from an antibody light and heavy chain, respectively. The variable binding regions are made up of discrete, well-defined sub-regions known as "complementarity determining regions" (CDRs) and "framework regions" (FRs). The terms "$C_L$" and "$C_H$" refer to an "immunoglobulin constant region," i.e., a constant region derived from an antibody light or heavy chain, respectively, with the latter region understood to be further divisible into $C_{H1}$, $C_{H2}$, $C_{H3}$ and $C_{H4}$ constant region domains, depending on the antibody isotype (IgA, IgD, IgE, IgG, IgM) from which the region was derived. A portion of the constant region domains makes up the Fc region (the "fragment crystallizable" region), which contains domains responsible for the effector functions of an immunoglobulin, such as ADCC (antibody-dependent cell-mediated cytotoxicity), CDC (complement-dependent cytotoxicity) and complement fixation, binding to Fc receptors, greater half-life in vivo relative to a polypeptide lacking an Fc region, protein A binding, and perhaps even placental transfer (see Capon et al. (1989) *Nature*, 337:525). Further, a polypeptide containing an Fc region allows for dimerization or multimerization of the polypeptide.

The domain structure of immunoglobulins is amenable to engineering, in that the antigen binding domains and the domains conferring effector functions may be exchanged between immunoglobulin classes and subclasses. Immunoglobulin structure and function are reviewed, for example, in Harlow et al., Eds., *Antibodies: A Laboratory Manual*, Chapter 14 (Cold Spring Harbor Laboratory, Cold Spring Harbor, 1988). An extensive introduction as well as detailed information about all aspects of recombinant antibody technology can be found in the textbook *Recombinant Antibodies* (John Wiley & Sons, NY, 1999). A comprehensive collection of detailed antibody engineering lab Protocols can be found in R. Kontermann and S. Dübel, Eds., *The Antibody Engineering Lab Manual* (Springer Verlag, Heidelberg/New York, 2000). Further related protocols are also available in *Current Protocols in Immunology* (August 2009) published by John Wiley & Sons, Inc., Boston, Mass.

Thus, this disclosure provides polynucleotides (isolated or purified or pure polynucleotides) encoding the proteins of interest of this disclosure for genetically modifying B cells, vectors (including cloning vectors and expression vectors) comprising such polynucleotides, and cells (e.g., host cells) transformed or transfected with a polynucleotide or vector according to this disclosure.

In certain embodiments, a polynucleotide (DNA or RNA) encoding a protein of interest of this disclosure is contemplated. Expression cassettes encoding proteins of interest are also contemplated herein.

The present disclosure also relates to vectors that include a polynucleotide of this disclosure and, in particular, to recombinant expression constructs. In one embodiment, this disclosure contemplates a vector comprising a polynucleotide encoding a protein of this disclosure, along with other polynucleotide sequences that cause or facilitate transcription, translation, and processing of such a protein-encoding sequences.

Appropriate cloning and expression vectors for use with prokaryotic and eukaryotic hosts are described, for example, in Sambrook et al., Molecular Cloning: A Laboratory Manual, Second Edition, Cold Spring Harbor, N.Y., (1989). Exemplary cloning/expression vectors include cloning vectors, shuttle vectors, and expression constructs, that may be based on plasmids, phagemids, phasmids, cosmids, viruses, artificial chromosomes, or any nucleic acid vehicle known in the art suitable for amplification, transfer, and/or expression of a polynucleotide contained therein.

As used herein, unless as otherwise described with regard to viral vectors, "vector" means a nucleic acid molecule capable of transporting another nucleic acid to which it has been linked. Exemplary vectors include plasmids, yeast artificial chromosomes, and viral genomes. Certain vectors can autonomously replicate in a host cell, while other vectors can be integrated into the genome of a host cell and thereby are replicated with the host genome. In addition, certain vectors are referred to herein as "recombinant expression vectors" (or simply, "expression vectors"), which contain nucleic acid sequences that are operatively linked to an expression control sequence and, therefore, are capable of directing the expression of those sequences.

In certain embodiments, expression constructs are derived from plasmid vectors. Illustrative constructs include modified pNASS vector (Clontech, Palo Alto, Calif.), which has nucleic acid sequences encoding an ampicillin resistance gene, a polyadenylation signal and a 17 promoter site; pDEF38 and pNEF38 (CMC ICOS Biologics, Inc.), which have a CHEF1 promoter; and pD18 (Lonza), which has a CMV promoter. Other suitable mammalian expression vectors are well known (see, e.g., Ausubel et al., 1995; Sambrook et al., supra; see also, e.g., catalogs from Invitrogen, San Diego, Calif.; Novagen, Madison, Wis.; Pharmacia, Piscataway, N.J.). Useful constructs may be prepared that include a dihydrofolate reductase (DHFR)-encoding sequence under suitable regulatory control, for promoting enhanced production levels of the fusion proteins, which levels result from gene amplification following application of an appropriate selection agent (e.g., methotrexate).

Generally, recombinant expression vectors will include origins of replication and selectable markers permitting transformation of the host cell, and a promoter derived from a highly-expressed gene to direct transcription of a downstream structural sequence, as described above. A vector in operable linkage with a polynucleotide according to this disclosure yields a cloning or expression construct. Exemplary cloning/expression constructs contain at least one expression control element, e.g., a promoter, operably linked to a polynucleotide of this disclosure. Additional expression control elements, such as enhancers, factor-specific binding sites, terminators, and ribosome binding sites are also contemplated in the vectors and cloning/expression constructs according to this disclosure. The heterologous structural sequence of the polynucleotide according to this disclosure is assembled in appropriate phase with translation initiation and termination sequences. Thus, for example, encoding nucleic acids as provided herein may be included in any one of a variety of expression vector constructs as a recombinant expression construct for expressing such a protein in a host cell.

The appropriate DNA sequence(s) may be inserted into a vector, for example, by a variety of procedures. In general, a DNA sequence is inserted into an appropriate restriction endonuclease cleavage site(s) by procedures known in the art. Standard techniques for cloning, DNA isolation, amplification and purification, for enzymatic reactions involving DNA ligase, DNA polymerase, restriction endonucleases and the like, and various separation techniques are contemplated. A number of standard techniques are described, for example, in Ausubel et al. (*Current Protocols in Molecular Biology*, Greene Publ. Assoc. Inc. & John Wiley & Sons, Inc., Boston, Mass., 1993); Sambrook et al. (*Molecular Cloning*, Second Ed., Cold Spring Harbor Laboratory, Plainview, N.Y., 1989); Maniatis et al. (*Molecular Cloning*, Cold Spring Harbor Laboratory, Plainview, N.Y., 1982); Glover (Ed.) (*DNA Cloning* Vol. I and II, IRL Press, Oxford, UK, 1985); Hames and Higgins (Eds.) (*Nucleic Acid Hybridization*, IRL Press, Oxford, UK, 1985); and elsewhere.

The DNA sequence in the expression vector is operatively linked to at least one appropriate expression control sequence (e.g., a constitutive promoter or a regulated promoter) to direct mRNA synthesis. Representative examples of such expression control sequences include promoters of eukaryotic cells or their viruses, as described above. Promoter regions can be selected from any desired gene using CAT (chloramphenicol transferase) vectors or other vectors with selectable markers. Eukaryotic promoters include CMV immediate early, HSV thymidine kinase, early and late SV40, LTRs from retrovirus, and mouse metallothionein-1. Selection of the appropriate vector and promoter is well within the level of ordinary skill in the art, and preparation of certain particularly preferred recombinant expression constructs comprising at least one promoter or regulated promoter operably linked to a nucleic acid encoding a protein or polypeptide according to this disclosure is described herein.

Variants of the polynucleotides of this disclosure are also contemplated. Variant polynucleotides are at least 60%, 65%, 70%, 75%, 80%, 85%, 90%, and preferably 95%, 96%, 97%, 98%, 99%, or 99.9% identical to one of the polynucleotides of defined sequence as described herein, or that hybridizes to one of those polynucleotides of defined sequence under stringent hybridization conditions of 0.015M sodium chloride, 0.0015M sodium citrate at about 65-68° C. or 0.015M sodium chloride, 0.0015M sodium citrate, and 50% formamide at about 42° C. The polynucleotide variants retain the capacity to encode a binding domain or fusion protein thereof having the functionality described herein.

The term "stringent" is used to refer to conditions that are commonly understood in the art as stringent. Hybridization stringency is principally determined by temperature, ionic strength, and the concentration of denaturing agents such as formamide. Examples of stringent conditions for hybridization and washing are 0.015M sodium chloride, 0.0015M sodium citrate at about 65-68° C. or 0.015M sodium chloride, 0.0015M sodium citrate, and 50% formamide at about 42° C. (see Sambrook et al., *Molecular Cloning: A Laboratory Manual,* 2nd Ed., Cold Spring Harbor Laboratory, Cold Spring Harbor, N.Y., 1989).

More stringent conditions (such as higher temperature, lower ionic strength, higher formamide, or other denaturing agent) may also be used; however, the rate of hybridization will be affected. In instances wherein hybridization of deoxyoligonucleotides is concerned, additional exemplary stringent hybridization conditions include washing in 6×SSC, 0.05% sodium pyrophosphate at 37° C. (for 14-base oligonucleotides), 48° C. (for 17-base oligonucleotides), 55° C. (for 20-base oligonucleotides), and 60° C. (for 23-base oligonucleotides).

A further aspect of this disclosure provides a host cell transformed or transfected with, or otherwise containing, any of the polynucleotides or vector/expression constructs of this disclosure. The polynucleotides or cloning/expression constructs of this disclosure are introduced into suitable cells using any method known in the art, including transformation, transfection and transduction. Host cells include the cells of a subject undergoing ex vivo cell therapy including, for example, ex vivo gene therapy. Eukaryotic host cells contemplated as an aspect of this disclosure when harboring a polynucleotide, vector, or protein according to this disclosure include, in addition to a subject's own cells (e.g., a human patient's own cells), VERO cells, HeLa cells, Chinese hamster ovary (CHO) cell lines (including modified CHO cells capable of modifying the glycosylation pattern of expressed multivalent binding molecules, see US Patent Application Publication No. 2003/0115614), COS cells (such as COS-7), W138, BHK, HepG2, 3T3, RIN, MDCK, A549, PC12, K562, HEK293 cells, HepG2 cells, N cells, 3T3 cells, *Spodoptera frugiperda* cells (e.g., Sf9 cells), *Saccharomyces cerevisiae* cells, and any other eukaryotic cell known in the art to be useful in expressing, and optionally isolating, a protein or peptide according to this disclosure. Also contemplated are prokaryotic cells, including *Escherichia coli, Bacillus subtilis, Salmonella typhimurium*, a Streptomycete, or any prokaryotic cell known in the art to be suitable for expressing, and optionally isolating, a protein or peptide according to this disclosure. In isolating protein or peptide from prokaryotic cells, in particular, it is contemplated that techniques known in the art for extracting protein from inclusion bodies may be used. The selection of an appropriate host is within the scope of those skilled in the art from the teachings herein. Host cells that glycosylate the fusion proteins of this disclosure are contemplated.

The term "recombinant host cell" (or simply "host cell") refers to a cell containing a recombinant expression vector. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

Recombinant host cells can be cultured in a conventional nutrient medium modified as appropriate for activating promoters, selecting transformants, or amplifying particular genes. The culture conditions for particular host cells selected for expression, such as temperature, pH and the like, will be readily apparent to the ordinarily skilled artisan. Various mammalian cell culture systems can also be employed to express recombinant protein. Examples of mammalian expression systems include the COS-7 lines of monkey kidney fibroblasts, described by Gluzman (1981) *Cell* 23:175, and other cell lines capable of expressing a compatible vector, for example, the C127, 3T3, CHO, HeLa and BHK cell lines. Mammalian expression vectors will comprise an origin of replication, a suitable promoter and, optionally, enhancer, and also any necessary ribosome binding sites, polyadenylation site, splice donor and acceptor sites, transcriptional termination sequences, and 5'-flanking nontranscribed sequences, for example, as described herein regarding the preparation of multivalent binding protein expression constructs. DNA sequences derived from the SV40 splice, and polyadenylation sites may be used to provide the required nontranscribed genetic elements. Introduction of the construct into the host cell can be effected by a variety of methods with which those skilled in the art will be familiar, including calcium phosphate transfection, DEAE-Dextran-mediated transfection, or electroporation (Davis et al. (1986) Basic Methods in Molecular Biology).

Compositions and Methods of Use

In one embodiment, the cell compositions of the present disclosure comprise a transduced and activated/differentiated B cell population expressing a protein of interest as described herein. In one embodiment, the compositions comprise transduced B cells that have differentiated into plasma B cells and express one or more proteins of interest. Target cell populations, such as the transduced and activated B cell populations of the present disclosure may be administered either alone, or as a pharmaceutical composition in combination with diluents and/or with other components such as cytokines or cell populations. Briefly, cell compositions of the present disclosure may comprise a transduced and activated/differentiated B cell population expressing a protein of interest as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present disclosure are preferably formulated for intravenous administration.

Cell compositions of the present disclosure may be administered in a manner appropriate to the disease to be treated (or prevented). The quantity and frequency of administration will be determined by such factors as the condition of the patient, and the type and severity of the patient's disease, although appropriate dosages may be determined by clinical trials.

When "an effective amount", "an anti-tumor effective amount", "a tumor-inhibiting effective amount", or "therapeutic amount" is indicated, the precise amount of the compositions of the present disclosure to be administered can be determined by a physician with consideration of individual differences in age, weight, tumor size, extent of infection or metastasis, and condition of the patient (subject). It can generally be stated that a cell composition comprising the B cells described herein may be administered at a dosage of $10^4$ to $10^7$ cells/kg body weight, preferably $10^5$ to $10^6$ cells/kg body weight, including all integer values within those ranges. B cell compositions may also be administered multiple times at these dosages. The cells can be administered by using infusion techniques that are commonly known in immunotherapy (see, e.g., Rosenberg et al., New Eng. J. of Med. 319:1676, 1988). The optimal dosage and treatment regime for a particular patient can readily be determined by one skilled in the art of medicine by monitoring the patient for signs of disease and adjusting the treatment accordingly.

Typically, in related adoptive immunotherapy studies, antigen-specific T cells are administered approximately at $2 \times 10^9$ to $2 \times 10^{11}$ cells to the patient. (See, e.g., U.S. Pat. No. 5,057, 423). In some aspects of the present disclosure, lower numbers of the transduced B cells of the present disclosure, in the range of $10^6$/kilogram ($10^6$-$10^{11}$ per patient) may be administered. In certain embodiments, the B cells are administered at $1 \times 10^5$, $1 \times 10^6$, $1 \times 10^7$, $1 \times 10^8$, $2 \times 10^8$, $2 \times 10^9$, $1 \times 10^{10}$, $2 \times 10^{10}$, $1 \times 10^{11}$, $5 \times 10^{11}$, or $1 \times 10^{12}$ cells to the subject. B cell compositions may be administered multiple times at dosages within these ranges. The cells may be autologous or heterologous to the patient undergoing therapy. If desired, the treatment may also include administration of mitogens (e.g., PHA) or lymphokines, cytokines, and/or chemokines (e.g., GM-CSF, IL-4, IL-13, Flt3-L, RANTES, MIP1α, etc.) as described herein to enhance induction of an immune response.

The administration of the subject compositions may be carried out in any convenient manner, including by aerosol inhalation, injection, ingestion, transfusion, implantation or transplantation. The compositions described herein may be administered to a patient subcutaneously, intradermally, intratumorally, intranodally, intramedullary, intramuscularly, by intravenous (i.v.) injection, or intraperitoneally. In one embodiment, the B cell compositions of the present disclosure are administered to a patient by intradermal or subcutaneous injection. In another embodiment, the B cell compositions as described herein are preferably administered by i.v. injection. The compositions of B cells may be injected directly into a tumor, lymph node, or site of infection.

In yet another embodiment, the pharmaceutical composition can be delivered in a controlled release system. In one embodiment, a pump may be used (see Langer, 1990, *Science* 249:1527-1533; Sefton 1987, *CRC Crit. Ref. Biomed. Eng.* 14:201; Buchwald et al., 1980; *Surgery* 88:507; Saudek et al., 1989, *N. Engl. J. Med.* 321:574). In another embodiment, polymeric materials can be used (see Medical Applications of Controlled Release, 1974, Langer and Wise (eds.), CRC Pres., Boca Raton, Fla.; Controlled Drug Bioavailability, Drug Product Design and Performance, 1984, Smolen and Ball (eds.), Wiley, New York; Ranger and Peppas, 1983; *J. Macromol. Sci. Rev. Macromol. Chem.* 23:61; see also Levy et al., 1985, *Science* 228:190; During et al., 1989, *Ann. Neurol.* 25:351; Howard et al., 1989, *J. Neurosurg.* 71:105). In yet another embodiment, a controlled release system can be placed in proximity of the therapeutic target, thus requiring only a fraction of the systemic dose (see, e.g., Medical Applications of Controlled Release, 1984, Langer and Wise (eds.), CRC Pres., Boca Raton, Fla., vol. 2, pp. 115-138).

The B cell compositions of the present disclosure may also be administered using any number of matrices. Matrices have been utilized for a number of years within the context of tissue engineering (see, e.g., Principles of Tissue Engineering (Lanza, Langer, and Chick (eds.)), 1997. The present disclosure utilizes such matrices within the novel context of acting as an artificial lymphoid organ to support and maintain the B cells. Accordingly, the present disclosure can utilize those matrix compositions and formulations which have demonstrated utility in tissue engineering. Accordingly, the type of matrix that may be used in the compositions, devices and methods of the disclosure is virtually limitless and may include both biological and synthetic matrices. In one particular example, the compositions and devices set forth by U.S. Pat. Nos. 5,980,889; 5,913,998; 5,902,745; 5,843,069; 5,787,900; or 5,626,561 are utilized. Matrices comprise features commonly associated with being biocompatible when administered to a mammalian host. Matrices may be formed from both natural or synthetic materials. The matrices may be non-biodegradable in instances where it is desirable to leave permanent structures or removable structures in the body of an animal, such as an implant; or biodegradable. The matrices may take the form of sponges, implants, tubes, telfa pads, fibers, hollow fibers, lyophilized components, gels, powders, porous compositions, or nanoparticles. In addition, matrices can be designed to allow for sustained release seeded cells or produced cytokine or other active agent. In certain embodiments, the matrix of the present disclosure is flexible and elastic, and may be described as a semisolid scaffold that is permeable to substances such as inorganic salts, aqueous fluids and dissolved gaseous agents including oxygen.

A matrix is used herein as an example of a biocompatible substance. However, the current disclosure is not limited to matrices and thus, wherever the term matrix or matrices appears these terms should be read to include devices and other substances which allow for cellular retention or cellular traversal, are biocompatible, and are capable of allowing traversal of macromolecules either directly through the substance such that the substance itself is a semi-permeable membrane or used in conjunction with a particular semi-permeable substance.

In certain embodiments of the present disclosure, B cells transduced and activated using the methods described herein, or other methods known in the art, are administered to a patient in conjunction with (e.g. before, simultaneously or following) any number of relevant treatment modalities, including but not limited to treatment with agents such as antiviral agents, chemotherapy, radiation, immunosuppressive agents, such as cyclosporin, azathioprine, methotrexate, mycophenolate, and FK506, antibodies, or other immunoablative agents such as CAMPATH, anti-CD3 antibodies or other antibody therapies, cytoxin, fludaribine, cyclosporin, FK506, rapamycin, mycophenolic acid, steroids, FR901228, cytokines, and irradiation. These drugs inhibit either the calcium dependent phosphatase calcineurin (cyclosporine and FK506) or inhibit the p70S6 kinase that is important for growth factor induced signaling (rapamycin). (Liu et al., Cell 66:807-815, 1991; Henderson et al., *Immun.* 73:316-321, 1991; Bierer et al., *Curr. Opin. Immun.* 5:763-773, 1993; Isoniemi (supra)). In a further embodiment, the cell compositions of the present disclosure are administered to a patient in conjunction with (e.g. before, simultaneously or following) bone marrow transplantation, T cell ablative therapy using either chemotherapy agents such as, fludarabine, external-beam radiation therapy (XRT), cyclophosphamide, or antibodies such as OKT3 or CAMPATH. In one embodiment, the cell compositions of the present disclosure are administered following B-cell ablative therapy such as agents that react with CD20, e.g. Rituxan®. For example, in one embodiment, subjects may undergo standard treatment with high dose chemotherapy followed by peripheral blood stem cell transplantation. In certain embodiments, following the transplant, subjects receive an infusion of the expanded immune cells of the present disclosure. In an additional embodiment, expanded cells are administered before or following surgery.

The dosage of the above treatments to be administered to a patient will vary with the precise nature of the condition being treated and the recipient of the treatment. The scaling of dosages for human administration can be performed according to art-accepted practices.

The transduced B cell compositions of the disclosure, particularly B cells transduced to express a particular antibody of interest, can be used in the treatment or prevention of various infectious diseases, cancers, degenerative diseases and immunological disorders.

Compositions comprising the transduced B cells as described herein may be used in treatment of any of a variety of infectious diseases caused by infectious organisms, such as viruses, bacteria, parasites and fungi. Infectious organisms may comprise viruses, (e.g., RNA viruses, DNA viruses, human immunodeficiency virus (HIV), hepatitis A, B, and C virus, herpes simplex virus (HSV), cytomegalovirus (CMV) Epstein-Barr virus (EBV), human papilloma virus (HPV)), parasites (e.g., protozoan and metazoan pathogens such as *Plasmodia* species, *Leishmania* species, *Schistosoma* species, *Trypanosoma* species), bacteria (e.g., *Mycobacteria*, in particular, *M. tuberculosis, Salmonella, Streptococci, E. coli, Staphylococci*), fungi (e.g., *Candida* species, *Aspergillus* species), *Pneumocystis carinii*, and prions (known prions infect animals to cause scrapie, a transmissible, degenerative disease of the nervous system of sheep and goats, as well as bovine spongiform encephalopathy (BSE), or "mad cow disease", and feline spongiform encephalopathy of cats. Four prion diseases known to affect humans are (1) kuru, (2) Creutzfeldt-Jakob Disease (CJD), (3) Gerstmann-Straussler-Scheinker Disease (GSS), and (4) fatal familial insomnia (FFI)). As used herein "prion" includes all forms of prions causing all or any of these diseases or others in any animals used—and in particular in humans and domesticated farm animals. Illustrative infectious diseases include, but are not limited to, toxoplasmosis, histoplasmosis, CMV, EBV, coccidiomycosis, tuberculosis, HIV, and the like.

In certain embodiments, the transduced B cell compositions as described herein may also be used for the prevention or treatment of a variety of cancers. In this regard, in certain embodiments, the compositions comprising transduced B cells are useful for preventing or treating melanoma, non-Hodgkin's lymphoma, Hodgkin's disease, leukemia, plasmocytoma, sarcoma, glioma, thymoma, breast cancer, prostate cancer, colo-rectal cancer, kidney cancer, renal cell carcinoma, uterine cancer, pancreatic cancer, esophageal cancer, brain cancer, lung cancer, ovarian cancer, cervical cancer, testicular cancer, gastric cancer, esophageal cancer, multiple myeloma, hepatoma, acute lymphoblastic leukemia (ALL), acute myelogenous leukemia (AML), chronic myelogenous leukemia (CML), and chronic lymphocytic leukemia (CLL), or other cancers.

In one embodiment, the transduced B cells may also be used in the treatment of immunological disorders such as acquired immune deficiency syndrome (AIDS), agammaglobulinemia, hypogammaglobulinemia, other immunodeficiencies, immunosuppression, and severe combined immunodeficiency disease (SCID).

In one embodiment, the transduced B cells as described herein may also be used in the treatment of autoimmune diseases such as, but not limited to, rheumatoid arthritis, multiple sclerosis, insulin dependent diabetes, Addison's disease, celiac disease, chronic fatigue syndrome, inflammatory bowel disease, ulcerative colitis, Crohn's disease, Fibromyalgia, systemic lupus erythematosus, psoriasis, Sjogren's syndrome, hyperthyroidism/Graves disease, hypothyroidism/Hashimoto's disease, Insulin-dependent diabetes (type 1), Myasthenia Gravis, endometriosis, scleroderma, pernicious anemia, Goodpasture syndrome, Wegener's disease, glomerulonephritis, aplastic anemia, paroxysmal nocturnal hemoglobinuria, myelodysplastic syndrome, idiopathic thrombocytopenic purpura, autoimmune hemolytic anemia, Evan's syndrome, Factor VIII inhibitor syndrome, systemic vasculitis, dermatomyositis, polymyositis and rheumatic fever.

Thus, in one embodiment, the methods herein include methods for treating a disease comprising administering to a subject or patient in need thereof a therapeutically effective amount of the compositions comprising the transduced B cells as described herein, thereby treating the disease.

EXAMPLES

Example 1

Transduction and Culture of PBMC-Derived B Cells to Produce Protein of Interest

In this example, PBMC-derived B cells were transduced and cultured to successfully produce the HIV neutralizing antibody, b12, or GFP.

Methods:

Human PBMCs were thawed in RPMI media and counted using a hemacytometer. B-cells were harvested from a total of $1.23 \times 10^7$ PBMCs using the easy-Sep B-cell negative selection B-cell purification kit as according to manufacturers protocols. Following purification, the cells were counted and $3.5 \times 10^5$ B-cells was added to two wells on a 24 well plate, with each well containing 1.25 ml of media. The media consisted of: RPMI, IL-2 (10 ng/ml), IL-10 (100 ng/ml), CpG (2 micromolar), and with or without PHA (4 micrograms/ml).

Additionally, $4 \times 10^4$ adherent mouse MS5 stromal cells that had been previously stably transduced with CD40-Ligand (MS40-Low cells) and selected for cells expressing low levels of the ligand were added to each of the wells and allowed to adhere to the culture plate for 24 hours prior to adding the B-cells (in the presence of the cytokines and RPMI).

The B-cells were exposed to these conditions for 3 days.

After 3 days in culture, the cells were removed and 1.6 micrograms of polybrene was added to each of the 1.25 ml cultures containing the B-cells and incubated for 3 hours and lenti-viral vectors pseudotyped with Edmonston-Measles virus, either encoding the HIV neutralizing antibody b12 or GFP (both under control of the EEK promoter; see Blood, 12 Feb. 2009, Vol. 113, No. 7, pp. 1422-1431 and published U.S. patent application 20100203630) were added to B-cells at an MOI of 30. In total, for both the plus and minus PHA conditions, a total of 2 wells of B-cells was transduced with b12 and 1 well with GFP.

Each well contained the media plus cytokines, MS40-Low cells and $2.67 \times 10^4$ B-cells. Fresh cytokines were added every 3 days and cells monitored using fluorescence microscopy for presence of GFP positive cells. Eighteen days post transduction, 500 microliters of culture media was removed from the b12 and GFP samples and tested for the presence of b12 using a Luminex device (Luminex Corporation, Austin, Tex.) using GP140 binding to measure for presence of b12 and purified b12 to generate a standard curve for quantitation. The Luminex results supported that PHA did not significantly impact production of b12, but was included in the protocol for accuracy in recounting methods.

Figure 1:
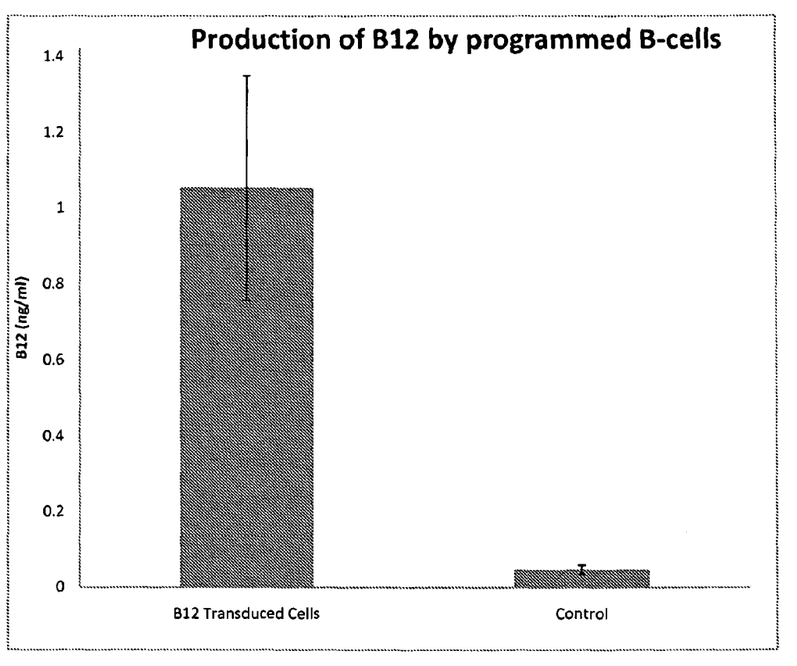
FIG. 1 is a bar graph showing production of the b12 antibody in transduced differentiated B cells.

Results:

The results indicated that the transduced cells produced on average 1.05 ng/ml of b12 antibody (see FIG. 1). Additionally, fluorescence microscopy showed that GFP transduced B cells were modified to glow green. It is important to note that the promoter used to drive GFP and b12 expression is only active in differentiated B cells. Therefore, the cells only fluoresce after they become plasma cells. Thus, this experiment showed both that the virus modified the cell correctly and that the culture system was able to differentiate the modified quiescent B cell into a plasma cell.

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety. All numerical ranges utilized herein explicitly include all integer values within the range and selection of specific numerical values within the range is contemplated depending on the particular use. Further, the following examples are offered by way of illustration, and not by way of limitation. From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A method for producing a protein of interest, comprising:
    (a) transducing in vitro a plurality of peripheral blood B cells with a retroviral vector pseudotyped with measles virus glycoproteins H and F to obtain a plurality of transduced B cells, wherein said retroviral vector comprises a nucleic acid of interest that encodes the protein of interest, the nucleic acid of interest being operably linked to a heterologous promoter that is capable of directing expression of the nucleic acid of interest in a plasma cell;
    (b) activating the plurality of transduced B cells to obtain a cell population comprising transduced B cells that have differentiated into CD38+ plasma cells, said step of activating comprising contacting the B cells with a composition comprising CD40L in combination with a B cell activating factor comprising one or more factors selected from IL-10, IL-4, IL-7, CpG DNA, IL-2, IL-15, IL-6, and IFN-α, wherein one of said factors is IL-15; and
    (c) culturing the CD38+ plasma cells of (b) so that the heterologous promoter directs expression of the nucleic acid of interest, and thereby producing the protein of interest.

2. The method of claim 1 wherein prior to the step of transducing, the plurality of B cells are resting B cells.

3. The method of claim 1 wherein the retroviral vector is a lentiviral vector.

4. The method of claim 3 wherein the lentiviral vector lacks lentivirus accessory genes.

5. The method of claim 1 wherein the plasma cells are characterized by cell surface expression of one or more markers selected from the group consisting of CD38, CD78, Interleukin-6 receptor, $CD27^{high}$, and CD138.

6. A method for producing a protein of interest, comprising:
    (a) activating in vitro a plurality of resting peripheral blood B cells to obtain a cell population comprising B cells that have differentiated into CD38+ plasma cells, said step of activating comprising contacting the B cells with a composition comprising CD40L in combination with a B cell activating factor comprising one or more factors selected from IL-10, IL-4, IL-7, CpG DNA, IL-2, IL-15, IL-6, and IFN-α, wherein one of said factors is IL-15;
    (b) transducing the cell population of (a) with a retroviral vector pseudotyped with measles virus glycoproteins H and F to obtain transduced CD38+ plasma cells, wherein said retroviral vector comprises a nucleic acid of interest that encodes the protein of interest, the nucleic acid of interest being operably linked to a heterologous promoter that is capable of directing expression of the nucleic acid of interest in a CD38+ plasma cell; and
    (c) culturing the transduced CD38+ plasma cells of (b) so that the heterologous promoter directs expression of the nucleic acid of interest, and thereby producing the protein of interest.

7. The method of claim 6 wherein the retroviral vector is a lentiviral vector.

8. The method of claim 7 wherein the lentiviral vector lacks lentivirus accessory genes.

9. The method of claim 6 wherein the nucleic acid of interest comprises a nucleic acid encoding at least an immunoglobulin VL and VH region.

10. The method of claim 6 wherein the nucleic acid of interest encodes an antibody protein or antigen-binding fragment thereof, a fusion protein, or a DNA-encoded small molecule.

11. The method of claim 10 wherein the antibody is an anti-human immunodeficiency virus (HIV) antibody, an anti-RNA antibody, or an antibody that binds a protein involved in immune regulation.

12. The method of claim 6 wherein the CD40L is provided on a cell or a cell line.

13. The method of claim 6 wherein the CD40L is bound to a tissue culture plate or a bead.

14. The method of claim 6 wherein the promoter is a B cell specific promoter.

15. The method of claim 6 wherein the promoter is an EEK promoter that comprises a human κ light chain promoter (Vκp) preceded by an intronic enhancer (iEκ), a matrix association region, and a 3' enhancer (3'Eκ).

* * * * *